(12) United States Patent
von dem Bruch

(10) Patent No.: US 12,168,644 B2
(45) Date of Patent: Dec. 17, 2024

(54) PROCESS FOR PREPARING 2-ALKOXY-4-AMINO-5-METHYL-PYRIDINES AND/OR 2-ALKOXY-4-ALKYLAMINO-5-METHYL-PYRIDINES

(71) Applicant: Saltigo GmbH, Leverkusen (DE)

(72) Inventor: Karsten von dem Bruch, Leverkusen (DE)

(73) Assignee: Saltigo GmbH, Leverkusen (DE)

( * ) Notice: Subject to any disclaimer, the term of this patent is extended or adjusted under 35 U.S.C. 154(b) by 736 days.

(21) Appl. No.: 17/415,783

(22) PCT Filed: Dec. 20, 2019

(86) PCT No.: PCT/EP2019/086760
§ 371 (c)(1),
(2) Date: Jun. 18, 2021

(87) PCT Pub. No.: WO2020/128020
PCT Pub. Date: Jun. 25, 2020

(65) Prior Publication Data
US 2022/0055992 A1 Feb. 24, 2022

(30) Foreign Application Priority Data
Dec. 21, 2018 (EP) .................................... 18215577

(51) Int. Cl.
*C07D 213/73* (2006.01)
(52) U.S. Cl.
CPC .................. *C07D 213/73* (2013.01)
(58) Field of Classification Search
CPC .................................................. C07D 213/73
See application file for complete search history.

(56) References Cited

U.S. PATENT DOCUMENTS

| | | |
|---|---|---|
| 8,877,741 B2 | 11/2014 | Fleck et al. |
| 8,895,585 B2 | 11/2014 | Fujiwara et al. |
| 9,561,228 B2 | 2/2017 | Haq et al. |
| 9,980,964 B2 * | 5/2018 | Haq ................... A61K 31/5377 |
| 2013/0196993 A1 | 8/2013 | Berger et al. |

FOREIGN PATENT DOCUMENTS

| | | | |
|---|---|---|---|
| WO | 2010016846 | * | 2/2010 |
| WO | 2017012647 A1 | | 1/2017 |

OTHER PUBLICATIONS

XP02790884 Database accession No. 72213525, Retrieved from: PubChem Compound [online] Dec. 27, 2013 (Dec. 27, 2013).
XP055583648, Saravanan Gowrisankar et al. "A General and Efficient Catalyst for Palladium—Catalyzed C-0 Coupling Reactions of Aryl Halides with Primary Alcohols", Journal of the American Chemical Society, vol. 132. No. 33. Aug. 25, 2010 (Aug. 25, 2010). pp. 11592-11598.
International Search Report from corresponding International Application No. PCT/EP2019/086760, dated Aug. 10, 2020, three pages.
Database Registry [Online] Feb. 24, 2014 (Feb. 24, 2014), Cap: "4-Pyridinamine, 5-methyl-2-propoxy-", XP093063164, found in STN Database accession No. 1553350-94-9.
Database Registry [Online] Feb. 19, 2014 (Feb. 19, 2014), Cap: "4-Pyridinamine, 2-(cyclopropylmethoxy)-5-methyl-", XP093063175, found in STN Database accession No. 1549016-49-0.
Database Registry [Online] Feb. 23, 2014 (Feb. 23, 2014), Cap: "4-Pyridinamine, 5-methyl-2-(phenylmethoxy)-", XP093063196, found in STN Database accession No. 1552820-82-2.
Erkin AV et al: "Synthesis and biological activity of hydrochlorides of benzyl ethers of pyrimidin-4(3H)-thiones and related compounds", Russian Journal of General Chemistry, vol. 85, No. 1, Feb. 17, 2015, pp. 79-87, XP035451420.

* cited by examiner

*Primary Examiner* — D Margaret M Seaman
(74) *Attorney, Agent, or Firm* — Nicanor A. Kohncke; Christopher L. McDavid; Alyson J. DiLena

(57) ABSTRACT

The present invention relates to a method for preparing 2-alkoxy-4-amino-5-methylpyridines of the formula (I) and/or 2-alkoxy-4-alkylamino-5-methylpyridines of the formula (II) from the corresponding 2-haloaminopyridines and the appropriate alcohols in the presence of base, and to the compounds resulting therefrom.

11 Claims, No Drawings

PROCESS FOR PREPARING 2-ALKOXY-4-AMINO-5-METHYL-PYRIDINES AND/OR 2-ALKOXY-4-ALKYLAMINO-5-METHYL-PYRIDINES

The present invention relates to a method for preparing 2-alkoxy-4-amino-5-methylpyridines of the formula (I) and/or 2-alkoxy-4-alkylamino-5-methylpyridines of the formula (II) from the corresponding 2-haloaminopyridines and the appropriate alcohols in the presence of base or the corresponding alkoxides, and to the compounds resulting therefrom.

2-Alkoxy-4-amino-5-methylpyridines and 2-alkoxy-4-alkylamino-5-methylpyridines are starting materials for the synthesis of pharmaceutical and agrochemical active ingredients. Such structural elements are found, for example, in acetyl-CoA carboxylase inhibitors in WO2014/114578 A2, which may be used in the treatment of diabetes or obesity for example. As active ingredients in WO 2014/124230 A2, such 2-alkoxy-4-amino-5-methylpyridines of the formula (I) are disclosed as starting materials in the preparation of active ingredients from the group of ERK kinase inhibitors, which may be used for the treatment of cancer.

To date, no method for preparing such 2-alkoxy-4-amino-5-methylpyridines and/or 2-alkoxy-4-alkylamino-5-methylpyridines is known from the literature.

There was therefore a need for a method for preparing 2-alkoxy-4-amino-5-methylpyridines of the formula (I) and/or 2-alkoxy-4-alkylamino-5-methylpyridines of the formula (II), with which these pyridine derivatives can be prepared in an efficient manner in industrial processes.

Surprisingly, a method for preparing 2-alkoxy-4-amino-5-methylpyridines of the formula (I) and/or 2-alkoxy-4-alkylamino-5-methylpyridines of the formula (II) has been found, which comprises the reaction of 2-halo-4-amino-5-methylpyridines of the formula (III) in the presence of alcohols and base to give these products in good yields and high purities.

The invention therefore relates to a method for preparing compounds of the formula (I)

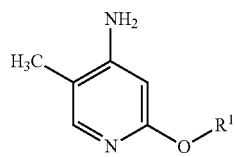

and/or compounds of the formula (II),

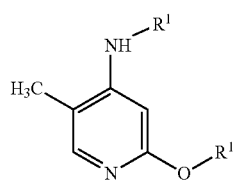

in which $R^1$ is linear or branched $C_1$-$C_{10}$-alkyl, preferably linear or branched $C_1$-$C_6$-alkyl which may be unsubstituted, monosubstituted or polysubstituted, or in which $R^1$ is $C_3$-$C_8$-cycloalkyl which may be unsubstituted, monosubstituted or polysubstituted, or in which $R^1$ is aralkyl, which may be unsubstituted, monosubstituted or polysubstituted, comprising at least the reaction of compounds of the formula (III),

in which X is Cl or Br, preferably Cl,
with a compound of the formula (IV),

$$R^1OH \quad (IV)$$

in which the radical $R^1$ has the definition specified for formula (I), in the presence of base and optionally in the presence of solvent.

In the compounds of the formula (II), the radicals $R^1$, in the substituent "O—$R^1$" at the 2-position of the pyridine ring and in the substituent "NH—$R^1$" at the 4-position of the pyridine ring, are preferably identical in one molecule. In the method according to the invention, if mixtures of compounds of the formulae (IV) and/or (V) having different $R^1$ radicals are used, compounds can also be produced comprising different $R^1$ radicals in one molecule.

Linear $C_1$-$C_{10}$-alkyl in accordance with $R^1$ is, for example, methyl, ethyl, n-propyl, n-butyl, n-pentyl, n-hexyl, n-heptyl, n-octyl, n-nonyl or n-decyl.

Unsubstituted linear or branched $C_1$-$C_{10}$-alkyl in accordance with radical $R^1$ is preferably methyl, ethyl, or n-propyl. Substituted linear alkyl in accordance with radical $R^1$ is preferably cyclopropylmethyl or 1,1-difluoroethyl.

Linear or branched $C_1$-$C_6$-alkyl in accordance with $R^1$ is, for example, methyl, ethyl, n-propyl, isopropyl, n-butyl, sec-butyl, isobutyl, n-pentyl, sec-pentyl, 3-pentyl, 2-methylbutyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2,3-dimethyl-2-butyl, 3,3-dimethyl-2-butyl or 3-ethyl-1-butyl.

The linear or branched $C_1$-$C_{10}$-alkyl or $C_1$-$C_6$-alkyl may be unsubstituted. It may also be monosubstituted or polysubstituted. Examples of monosubstituted $C_1$-$C_6$-alkyl are 2-methoxy-1-ethyl, 2-ethoxy-1-ethyl, 3-methoxy-1-propyl, 3-ethoxy-1-propyl or 1-cyclopropylmethyl, 1-cyclopropylethyl, 1-cyclobutylethyl, 1-cyclopentylethyl, 1-cyclohexylethyl, 2-cyclopropylethyl, 2-cyclobutylethyl, 2-cyclopentylethyl, 2-cyclohexylethyl, 1,1-difluoroethyl or 2,2-difluorocyclopropylmethyl.

$C_3$-$C_8$-cycloalkyl in accordance with $R^1$ is, for example, cyclopropyl, cyclobutyl, cyclopentyl, cyclohexyl, cycloheptyl or cyclooctyl.

$C_3$-$C_8$-cycloalkyl may also be unsubstituted, monosubstituted or polysubstituted. Example of monosubstituted $C_3$-$C_8$-cycloalkyl are 2-methylcyclobutyl, 3-methylcyclobutyl, 2-methylcyclopentyl, 3-methylcyclopentyl, 2-methylcyclohexyl, 3-methylcyclohexyl, 4-methylcyclohexyl, 2-methylcycloheptyl, 3-methylcycloheptyl, 4-methylcycloheptyl, 2-ethylcyclobutyl, 3-ethylcyclobutyl, 2-ethylcyclopentyl, 3-ethylcyclopentyl, 2-ethylcyclohexyl, 3-ethylcyclohexyl, 4-ethylcyclohexyl, 2-propylcyclobutyl, 3-propylcyclobutyl, 2-propylcyclopentyl, 3-propylcyclopentyl, 2-butylcyclobutyl, 3-butylcyclobutyl, 2-hydroxycyclopropyl, 2-fluorocyclopropyl.

Aralkyl in accordance with $R^1$ comprises both alkyl radicals which have been substituted by aromatic or by heteroaromatic radicals and is, for example, benzyl, phenethyl, 2-furylmethyl, 3-furylmethyl, 2-pyridylmethyl, 3-pyridylmethyl, 4-pyridylmethyl, 1-naphthylmethyl or 2-naphthylmethyl. Aralkyl in accordance with $R^1$ is preferably benzyl, 2-furylmethyl, 3-furylmethyl or 3-pyridylmethyl.

In the method according to the invention, the base is selected from alkali metal hydroxides, alkaline earth metal hydroxides, alkali metal carbonates or alkaline earth metal carbonates or compounds of the formula (V)

$$R^1OM \qquad (V),$$

in which the radical $R^1$ has the definition specified for formula (I), and M is an alkali metal, particularly potassium or sodium, particularly preferably sodium, or mixtures thereof. In the method according to the invention, the base can be used both in solid or liquid form, as pure substance, and in liquid media in dissolved or suspended form. The alkali metal alkoxides of the formula (V) used in the reaction are typically used in the form of their alcoholic solutions or without solvent.

The method according to the invention is typically carried out in the presence of solvent. In this case, undissolved constituents may arise in the reaction mixture at the start, during or at the end of the reaction. Suitable as solvents are toluene, o-, m-, p-xylene, ethylbenzene, ethoxybenzene, compounds of the formula (IV), water or mixtures thereof. For the method according to the invention, the solvent used is preferably toluene, p-xylene or the compounds of the formula (IV), water or mixtures thereof.

The reaction partners, i.e. the compounds of the formula (III) and the compounds of the formula (IV), are reacted in the method according to the invention at temperatures, for example, of 100 to 180° C., preferably 120 to 160° C. In this case, the reaction partners can be initially mixed individually or separately, either as pure substance or dissolved or suspended in solvent at room temperature. Subsequently, the reaction mixture can be heated to the required reaction temperature, wherein the solvent may or may not be distilled off in a simultaneous and/or phased manner. In a further embodiment of the method according to the invention, the base, together with the mixture of the compound of the formula (III) with the solvent, may already be heated to a temperature above ambient temperature and then the compound of the formula (IV) is added. The addition is carried out, for example, in portions or continuously. Preferably, the compound of the formula (IV) is added continuously.

In a preferred embodiment, the method according to the invention is carried out such that in a step a) at least the base, preferably compounds of the formula (V), for example as a solution in the corresponding alcohol or without solvent, and optionally solvent, are initially charged, and in a step b) the compound of the formula (III) is added to the mixture of step a), added as a solution or without solvent, at temperatures of 0 to 170° C., preferably 20 to 160° C., and the mixture resulting from step b) is reacted in a step c) at temperatures of 120 to 170° C., preferably 130 to 160° C. The compound of the formula (III) is typically added in one step, in two or more steps or continuously.

Typically, the method according to the invention is carried out such that 1 to 10 mol, preferably 1 to 6 mol, particularly preferably 2 to 4 mol of the compound of the formula (IV) are used per mole of compound of the formula (III).

Also typically in the method according to the invention, 1.5 to 6 mol, preferably 2 to 5 mol, particularly preferably 2.5 to 4 mol of the base are used per mole of compound of the formula (III).

In the method according to the invention, for example in a step a), at least the base selected from compound of the formula (V), NaOH or KOH, preferably as a solution in the corresponding alcohol or without solvent, an alcohol of the formula (IV) and optionally solvent may be initially charged. In a step b), the compound of the formula (III), optionally as a mixture with the compound of the formula (IV), may be added to the mixture of step a) at temperatures of 120 to 170° C., preferably 130 to 160° C. The compound of the formula (III) is typically added in one step, in two or more steps or continuously. The mixture resulting from step b) may be reacted at temperatures of 120 to 170° C., preferably 130 to 160° C. In this case, the solvent may or may not be distilled off in a simultaneous and/or phased manner. Typically, the steps a), b) and c) are carried out successively.

In the method according to the invention and in a further preferred embodiment, for example, the base, optionally solvent and compound of the formula (III) are mixed and this mixture is heated to 120 to 170° C., preferably 130 to 160° C. In this case, the solvent may or may not be distilled off in a simultaneous and/or phased manner. The reaction mixture is preferably maintained at this temperature until no further reaction takes place. The chemical reaction is typically monitored by gas chromatography, thin-layer chromatography, infrared spectroscopy or HPLC.

In the method according to the invention, preferably and by way of example, at least the base, selected from compound of the formula (V), NaOH or KOH, solvent selected from toluene, o-, m-, p-xylene, ethylbenzene, ethoxybenzene or water, and the compound of the formula (IV) are initially mixed, preferably at ambient temperature, and this mixture is heated to 120 to 170° C., preferably 130 to 160° C. If the compound of the formula (V) is used as base, the compound of the formula (IV), which comprises radical $R^1$ identical to formula (V), is preferably used as solvent. In this embodiment, for example, in the case of sodium benzyloxide as base, benzyl alcohol is used as solvent.

In the method according to the invention, for example, at least the compound of the formula (III) and optionally the solvent are initially charged and then the base and the compound of the formula (IV) are added. During the addition, the base may be present either as pure substance, in dissolved form or suspended form.

The method according to the invention is preferably carried out such that at least the compound of the formula (III) and solvent selected from toluene, o-, m-, p-xylene, ethylbenzene, ethoxybenzene, are initially charged and then the compound of the formula (V) as base and the compound of the formula (IV) are added. During the reaction in the method according to the invention, a liquid phase is preferably distilled off. In this case, the distillation during the reaction can be carried out at ambient pressure, elevated or reduced pressure. The distillation during the reaction is preferably carried out at a pressure of 0.0001 to 0.1 MPa. A person skilled in the art typically selects the pressure depending on the boiling point of the solvent and the reaction temperature required.

If the reaction temperature is above the boiling point of the reaction mixture or the individual components of the reaction mixture at ambient pressure, the reaction is typically carried out in pressure-tight apparatuses, for example in autoclaves, under elevated autogenous pressure or under pressure by nitrogen for example.

The method according to the invention is preferably carried out in the absence of copper compounds, for example in the absence of copper iodide. In an alternative embodiment, the method according to the invention is carried out in the absence of catalysts, for example in the absence of transition metal compounds. Surprisingly, using the method according to the invention, the compounds of the formula (I) and/or the compounds of the formula (II) are obtained in high yields even in the absence of copper compounds, for example copper iodide, and/or in the absence of catalysts, for example transition metal compounds.

After completion of the reaction of the compound of the formula (III), the reaction products, i.e. the compounds of the formula (I) and/or the compounds of the formula (II), are obtained from the reaction mixture, for example, by a) adding water to the reaction mixture, which has been controlled to a temperature of ambient temperature up to reaction temperature, preferably cooled to 15° C. to 100° C., and
b) adding acid, for example hydrochloric acid, adjusting the pH of the mixture, for example to pH 7 to 9, and
c) adding water and a solvent sparingly miscible with water, for example toluene or xylene, to the mixture and mixing the resulting mixture, and
d) subsequently, after phase separation, isolating the organic phase, optionally washing with water and then optionally freeing said organic phase from water, and
e) then removing the volatile constituents of the organic phase, for example by distillation, the crude product being obtained, and
f) subsequently isolating the product from the crude product either by fractional distillation or crystallization.

In this variant, after step a) and prior to step b)—if the method according to the invention has been carried out in the presence of solvent of the formula (IV)—the solvent of the formula (IV) is removed from the reaction mixture, for example by distillation. In a further variant, for example—if the method according to the invention has been carried out in the presence of solvent of the formula (IV), a) the pH of the reaction mixture is adjusted by adding acid, for example hydrochloric acid, for example to pH 7 to 9, and
b) then further solvent of the formula (IV), for example ethanol, is added to the reaction mixture, whereby the product may precipitate as a solid, and
c) subsequently the reaction mixture is freed from volatile constituents, for example by distillation, whereby the crude product is obtained, and
d) then optionally the product is isolated from the crude product either by fractional distillation or crystallization.

In a further variant, the compounds of the formula (I) and/or the compounds of the formula (II) are separated off from the reaction mixture, for example by a) separating off the crude product precipitated as a solid, preferably by filtration, from the reaction mixture, which has been controlled to a temperature of ambient temperature up to reaction temperature, preferably cooled to 15° C. to 70° C., and
b) then optionally isolating the product from the crude product either by fractional distillation or crystallization.

In this variant, prior to step a), a solvent, for example ethanol, may optionally be added to the reaction mixture, which has been controlled to a temperature of ambient temperature up to reaction temperature, preferably cooled to 15° C. to 70° C. Also in this case, prior to step a), optionally by adding acid, for example hydrochloric acid, the pH of the mixture may be adjusted, for example to pH 7 to 9.

The invention also includes compounds of the formula (I) or formula (II) which are obtained by the method according to the invention.

The invention preferably includes compounds of the formula (I),

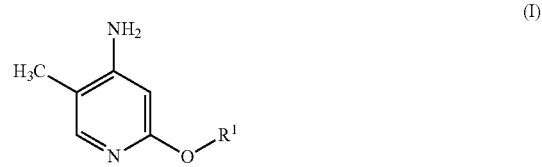

in which $R^1$ is linear or branched $C_1$-$C_6$-alkyl, preferably $C_3$-$C_6$-alkyl, or is a radical selected from the group comprising methyl, ethyl, n-propyl, isopropyl, n-butyl, sec-butyl, isobutyl, n-pentyl, sec-pentyl, 3-pentyl, 2-methyl-1-butyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2,3-dimethyl-2-butyl, 3,3-dimethyl-2-butyl or 3-ethyl-1-butyl, wherein the linear or branched $C_1$-$C_6$-alkyl may be unsubstituted, monosubstituted or polysubstituted, or in which $R^1$ is $C_3$-$C_8$-cycloalkyl selected from the group comprising cyclopropyl, cyclobutyl, cyclopentyl, cyclohexyl, cycloheptyl, cyclooctyl, 2-methylcyclobutyl, 3-methylcyclobutyl, 2-methylcyclopentyl, 3-methylcyclopentyl, 2-methylcyclohexyl, 3-methylcyclohexyl, 4-methylcyclohexyl, 2-methylcycloheptyl, 3-methylcycloheptyl, 4-methylcycloheptyl, 2-ethylcyclobutyl, 3-ethylcyclobutyl, 2-ethylcyclopentyl, 3-ethylcyclopentyl, 2-ethylcyclohexyl, 3-ethylcyclohexyl, 4-ethylcyclohexyl, 2-propylcyclobutyl, 3-propylcyclobutyl, 2-propylcyclopentyl, 3-propylcyclopentyl, 2-butylcyclobutyl, 3-butylcyclobutyl, 2-hydroxycyclopropyl or 2-fluorocyclopropyl, wherein the $C_3$-$C_8$-cycloalkyl may be unsubstituted, monosubstituted or polysubstituted, or in which $R^1$ is aralkyl, preferably benzyl, phenethyl, 2-furylmethyl, 3-furylmethyl, 2-pyridylmethyl, 3-pyridylmethyl, 4-pyridylmethyl, 1-naphthylmethyl or 2-naphthylmethyl, which may be unsubstituted, monosubstituted or polysubstituted.

These compounds of the formula (I) are accessible in high yields and purities by the method according to the invention described above.

The invention preferably also includes compounds of the formula (II),

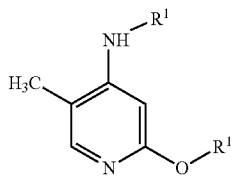

(II)

in which R¹ is linear or branched $C_1$-$C_6$-alkyl, preferably $C_3$-$C_6$-alkyl, or is a radical selected from the group comprising methyl, ethyl, n-propyl, isopropyl, n-butyl, sec-butyl, isobutyl, n-pentyl, sec-pentyl, 3-pentyl, 2-methyl-1-butyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2,3-dimethyl-2-butyl, 3,3-dimethyl-2-butyl, 3-ethyl-1-butyl, wherein the linear or branched $C_3$-$C_6$-alkyl may be unsubstituted, monosubstituted or polysubstituted, or in which R¹ is $C_3$-$C_8$-cycloalkyl selected from the group comprising cyclopropyl, cyclobutyl, cyclopentyl, cyclohexyl, cycloheptyl, cyclooctyl, 2-methylcyclobutyl, 3-methylcyclobutyl, 2-methylcyclopentyl, 3-methylcyclopentyl, 2-methylcyclohexyl, 3-methylcyclohexyl, 4-methylcyclohexyl, 2-methylcycloheptyl, 3-methylcycloheptyl, 4-methylcycloheptyl, 2-ethylcyclobutyl, 3-ethylcyclobutyl, 2-ethylcyclopentyl, 3-ethylcyclopentyl, 2-ethylcyclohexyl, 3-ethylcyclohexyl, 4-ethylcyclohexyl, 2-propylcyclobutyl, 3-propylcyclobutyl, 2-propylcyclopentyl, 3-propylcyclopentyl, 2-butylcyclobutyl, 3-butylcyclobutyl, 2-hydroxycyclopropyl or 2-fluorocyclopropyl, wherein the $C_1$-$C_8$-cycloalkyl may be unsubstituted, monosubstituted or polysubstituted, or in which R¹ is aralkyl, preferably benzyl, phenethyl, 2-furylmethyl, 3-furylmethyl, 2-pyridylmethyl, 3-pyridylmethyl, 4-pyridylmethyl, 1-naphthylmethyl or 2-naphthylmethyl, which may be unsubstituted, monosubstituted or polysubstituted.

These compounds of the formula (II) are accessible by the method according to the invention described above. Typically, higher yields of the compounds of the formula (II) are obtained in which the radical R¹ is less sterically challenging, for example methyl or ethyl, when either all components of the reaction, namely the compound of the formula (I), the compound of the formula (IV) in its function as solvent, the compound of the formula (V) as base and as reactant, are mixed preferably at ambient temperature and the mixture is then heated to 120 to 170° C., preferably 130 to 160° C. If the radical R¹ to be introduced is more sterically challenging, for example benzyl, higher yields of the compounds of the formula (II) are then obtained, for example, when the compound of the formula (III), optionally dissolved in the corresponding alcohol of the formula (IV), is added to a solution of the alkoxide of the formula (V) at a temperature of 120 to 170° C., preferably 130 to 160° C.

Particular preference is given to compounds of formula (I)

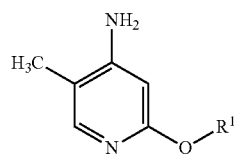

(I)

and/or of the formula (II),

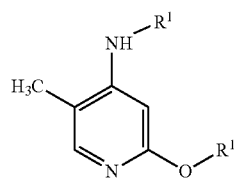

(II)

in which R¹ is methyl, ethyl, n-propyl, isopropyl, cyclopropylmethyl, 2,2-difluorocyclopropylmethyl, benzyl, 1-methoxyethoxy or 1,1-difluoroethyl.

EXAMPLES

Example 1a: Preparation of 4-amino-2-benzyloxy-5-methylpyridine/4-benzylamino-2-benzyloxy-5-methylpyridine (Inventive)

A mixture of 60 g (0.55 mol) of benzyl alcohol and 40 g (0.22 mol) of a 30% methanolic sodium methoxide solution was heated to ca. 150° C. and the methanol produced was distilled off. After reaching 150° C., a vacuum of 90 mbar was applied with continuous removal of distillate and the mixture was stirred under these conditions for a further 1 hour. Subsequently, the vacuum was improved at 150° C. until distillation began. Distillation continued under these conditions until the top temperature reached or exceeded 100° C.

At 150° C. and under standard pressure, the solution of 10 g (0.07 mol) of 4-amino-2-chloro-5-methylpyridine in 20 g (0.18 mol) of benzyl alcohol was then metered in over 2 hours. After metering, the reaction mixture was stirred further at 150° C. until conversion was complete.

After cooling to room temperature and addition of 40 g of water and 60 g of toluene, the mixture was acidified to pH 9 with 30% aqueous hydrochloric acid. The organic phase remaining after removal of the aqueous phase was washed once with 40 g of water.

After concentration of the organic phase under reduced pressure up to a bottom temperature of 140° C. and 10 mbar, 18 g of a beige oil comprising 40% by weight 4-amino-2-benzyloxy-5-methylpyridine (0.03 mol) and 55% by weight 4-benzylamino-2-benzyloxy-5-methylpyridine (0.03 mol) (48% and 46% theoretical yield respectively) remained. ¹H-NMR and GC-MS verify the chemical structures.

Example 1b: Preparation of 4-amino-2-benzyloxy-5-methylpyridine/4-benzylamino-2-benzyloxy-5-methylpyridine (Inventive)

A mixture of 60 g (0.55 mol) of benzyl alcohol and 9 g (0.22 mol) of sodium hydroxide was heated to ca. 150° C.

with distillate removal. After reaching 150° C., a vacuum of 90 mbar was applied with continuous removal of distillate and the mixture was stirred under these conditions for a further 1 hour. Subsequently, the vacuum was improved at 150° C. until distillation began. Distillation continued under these conditions until the top temperature reached or exceeded 100° C.

At 150° C. and under standard pressure, the solution of 10 g (0.07 mol) of 4-amino-2-chloro-5-methylpyridine in 20 g (0.18 mol) of benzyl alcohol was then metered in over 2 hours. After metering, the reaction mixture was stirred further at 150° C. until conversion was complete.

After cooling to room temperature and addition of 40 g of water and 60 g of toluene, the mixture was acidified to pH 9 with 30% aqueous hydrochloric acid. The organic phase remaining after removal of the aqueous phase was washed once with 40 g of water.

After concentrating the organic phase under reduced pressure up to 140° C. bottom temperature and 10 mbar, 17 g of a beige oil comprising 45% by weight 4-amino-2-benzyloxy-5-methylpyridine (0.04 mol) and 49% by weight 4-benzylamino-2-benzyloxy-5-methylpyridine (0.03 mol) (53% and 40% theoretical yield respectively) remained.

Example 1c: Preparation of 4-amino-2-benzyloxy-5-methylpyridine/4-benzylamino-2-benzyloxy-5-methylpyridine (Inventive)

A mixture of 60 g (0.55 mol) of benzyl alcohol and 18 g (0.22 mol) of an aqueous 50% sodium hydroxide solution was heated to ca. 150° C. with distillate removal. After reaching 150° C., a vacuum of 90 mbar was applied with continuous removal of distillate and the mixture was stirred under these conditions for a further 1 hour. Subsequently, the vacuum was improved at 150° C. until distillation began. Distillation continued under these conditions until the top temperature reached or exceeded 100° C.

At 150° C. and under standard pressure, the solution of 10 g (0.07 mol) of 4-amino-2-chloro-5-methylpyridine in 20 g (0.18 mol) of benzyl alcohol was then metered in over 2 hours. After metering, the reaction mixture was stirred further at 150° C. until conversion was complete.

After cooling to room temperature and addition of 40 g of water and 60 g of toluene, the mixture was acidified to pH 9 with 30% aqueous hydrochloric acid. The organic phase remaining after removal of the aqueous phase was washed once with 40 g of water.

After concentrating the organic phase under reduced pressure up to 140° C. bottom temperature and 10 mbar, ca. 17 g of a beige oil comprising 60% by weight 4-amino-2-benzyloxy-5-methylpyridine (0.05 mol) and 35% by weight 4-benzylamino-2-benzyloxy-5-methylpyridine (0.02 mol) (65% and 28% theoretical yield respectively) remained.

Example 1d: Preparation of 4-amino-2-benzyloxy-5-methylpyridine (Inventive)

A mixture of 57.5 g (0.53 mol) of benzyl alcohol, 65 g (0.61 mol) of xylene, 19 g (0.47 mol) of sodium hydroxide and 25 g (0.18 mol) of 4-amino-2-chloro-5-methylpyridine was heated to 147° C. at standard pressure with distillate removal and the mixture was further stirred at this temperature until conversion was complete.

After cooling to ca. 100° C., the distillate produced and also 20 g of xylene and 60 g of water were added and the mixture was controlled to a temperature of ca. 60° C. After removing the lower phase at ca. 60° C., the remaining organic phase was washed once with 75 g of water.

After concentrating the organic phase under reduced pressure up to 60° C. bottom temperature and 20 mbar, ca. 79 g of a beige liquid comprising 40% by weight 4-amino-2-benzyloxy-5-methylpyridine (0.15 mol, 88% theoretical yield) remained. The ratio of 4-amino-2-benzyloxy-5-methylpyridine to 4-benzylamino-2-benzyloxy-5-methylpyridine was ca. 98:2.

Example 1e: Preparation of 4-amino-2-benzyloxy-5-methylpyridine (Inventive)

23 g (0.21 mol) of benzyl alcohol were heated to ca. 120° C. At ca. 120° C. and under standard pressure, the solution of 10 g (0.07 mol) of 4-amino-2-chloro-5-methylpyridine in 53 g of methanol was metered in over 2-3 hours so that the methanol was rapidly distilled off. After metering, distillation was continued with heating at an internal temperature of ca. 120° C. until no more distillate accrued.

After addition of 24 g of xylene and 14.2 g (0.18 mol) of an aqueous 50% sodium hydroxide solution, the mixture was heated slowly to 144° C. and the resulting aqueous phase in the biphasic distillate was separated out. Subsequently, this was adjusted to full distillate removal and the mixture further heated to 147° C.

The reaction mixture was stirred at 147° C. for 16 hours, then cooled to 90-100° C. and 13 g of xylene and 26 g of demineralized water were added. After cooling to ca. 60° C., the aqueous phase was removed and 30 g of demineralized water were added to the organic phase. After acidifying with 30% aqueous hydrochloric acid to pH 8-9, the aqueous phase was again removed.

After concentrating the organic phase under reduced pressure up to 60° C. bottom temperature and 100 mbar, ca. 54 g of a red-brown liquid comprising ca. 26% by weight 4-amino-2-benzyloxy-5-methylpyridine (0.07 mol) and 1.7% by weight 4-benzylamino-2-benzyloxy-5-methylpyridine (3 mmol) (93% and 4% theoretical yield respectively) remained.

Example 2a: Preparation of 4-amino-2-ethoxy-5-methylpyridine (Inventive)

In an autoclave, the mixture of 12 g (0.08 mol) of 4-amino-2-chloro-5-methylpyridine and 144 g (0.42 mol) of a 20% ethanolic solution of sodium ethoxide was heated to 170° C. under autogenous pressure and the mixture was stirred under these conditions for 15 hours.

After cooling to room temperature, the reaction mixture was neutralized with 30% aqueous hydrochloric acid and 120 g of ethanol were added. The precipitated solid was filtered off and the mother liquor was concentrated to dryness. The solid remaining after evaporating the mother liquor was taken up in methylene chloride and insoluble fractions were filtered off. The mother liquor was again concentrated to dryness. There remained ca. 8.4 g of a beige oil comprising 85% by weight 4-amino-2-ethoxy-5-methylpyridine (0.05 mol) in addition to 10% by weight 4-ethylamino-2-ethoxy-5-methylpyridine (4 mmol) (55% and 5% theoretical yield respectively).

The crude product was further purified by recrystallization from tert-butyl methyl ether/n-hexane. This gave a pale beige solid having a content of ca. 95% by weight 4-amino-2-ethoxy-5-methylpyridine.

Example 2b: Preparation of 4-amino-2-ethoxy-5-methylpyridine (Inventive)

120 g (0.35 mol) of a 20% ethanolic solution of sodium ethoxide was added over ca. 2 hours to a mixture of 25.2 g (0.18 mol) of 4-amino-2-chloro-5-methylpyridine and 86 g (0.70 mol) of phenetol with distillate removal at 120° C. After metering, the mixture was heated to 170° C. and stirred at this temperature until full conversion.

After cooling to room temperature, 150 g of tert-butyl methyl ether and 150 g of water were added to the reaction mixture and the aqueous phase removed. 150 g of water was added to the organic phase and the resulting mixture was adjusted to pH 8-9 with 30% aqueous hydrochloric acid. After separating off the aqueous phase, the organic phase was concentrated to dryness at 50° C. and 20 mbar.

There remained ca. 88 g of a brown oil, which was purified by fractional distillation under reduced pressure. The highest-boiling fraction gave 16 g of a colorless liquid which on cooling immediately solidified to give a colorless solid comprising 94% by weight 4-amino-2-ethoxy-5-methylpyridine (0.10 mol) and 4% by weight 4-ethylamino-2-ethoxy-5-methylpyridine (3 mmol) (56% and 2% theoretical yield respectively).

The product fraction was further purified by recrystallization from n-hexane in a yield of 97% of theoretical yield and was largely freed from 4-ethylamino-2-ethoxy-5-methylpyridine.

Example 2c: Preparation of 4-amino-2-ethoxy-5-methylpyridine (Inventive)

In an autoclave, the mixture of 40 g (0.28 mol) of 4-amino-2-chloro-5-methylpyridine, 146 g (3.0 mol) of ethanol and 43 g (1.1 mol) of sodium hydroxide was heated to 145° C. under autogenous pressure and the mixture was stirred under these conditions for 16 hours.

After cooling to room temperature, 150 g of water were added to the reaction mixture which was freed from alcohol by distillation at standard pressure up to a bottom temperature of ca. 100° C. 150 g of toluene were added to the distillation bottoms and controlled at a temperature of ca. 50° C. The aqueous phase was separated off at this temperature.

After addition of a further 150 g of water, the resulting mixture was adjusted to pH 8-9 with 30% aqueous hydrochloric acid. Subsequently, at standard pressure, the toluene was separated out and after cooling to room temperature the precipitated solid was filtered off and this was washed once with 100 g of water. After drying under reduced pressure, this gave 36 g of colorless to pale beige solid having a purity of ca. 99.8% by weight (0.24 mol, corresponds to 85% theoretical yield).

Example 3: Preparation of 4-amino-2-propoxy-5-methylpyridine (Inventive)

In an autoclave, the mixture of 24 g (0.17 mol) of 4-amino-2-chloro-5-methylpyridine, 120 g (2.0 mol) of n-propanol and 25.8 g (0.65 mol) of sodium hydroxide was heated to 145° C. under autogenous pressure and the mixture was stirred under these conditions for 24 hours.

After cooling to room temperature, 150 g of water were added to the reaction mixture which was freed from alcohol by distillation at standard pressure up to a bottom temperature of ca. 110° C. 90 g of toluene were added to the distillation bottoms and controlled at a temperature of ca. 50° C. The aqueous phase was separated off at this temperature.

After addition of a further 90 g of water, the resulting mixture was adjusted to pH 8-9 with 30% aqueous hydrochloric acid. Subsequently, the toluene was separated out at standard pressure and 12 g of isopropanol were added to the remaining suspension at ca. 70° C. After cooling to room temperature, the precipitated solid was filtered off and washed once with 60 g of water.

After drying under reduced pressure, this gave 24.4 g of a colorless to pale beige solid having a purity of 99% by weight (0.15 mol, corresponds to 88% theoretical yield).

Example 4: Preparation of 4-amino-2-isopropoxy-5-methylpyridine (Inventive)

In an autoclave, the mixture of 24 g (0.17 mol) of 4-amino-2-chloro-5-methylpyridine, 120 g (2.0 mol) of isopropanol and 25.8 g (0.65 mol) of sodium hydroxide was heated to 145° C. under autogenous pressure and the mixture was stirred under these conditions for 24 hours.

After cooling to room temperature, 100 g of water were added to the reaction mixture which was freed from alcohol by distillation at standard pressure up to a bottom temperature of ca. 110° C. 90 g of toluene were added to the distillation bottoms and controlled at a temperature of ca. 50° C. The aqueous phase was separated off at this temperature.

After addition of a further 90 g of water, the resulting mixture was adjusted to pH 8-9 with 30% aqueous hydrochloric acid. Subsequently, the toluene was separated out at standard pressure and 12 g of isopropanol were added to the remaining suspension at ca. 70° C. After cooling to room temperature, the precipitated solid was filtered off and washed once with 60 g of water.

After drying under reduced pressure, this gave 18.1 g of a colorless to pale beige solid having a purity of 99.1% by weight (0.11 mol, corresponds to 65% theoretical yield).

What is claimed is:

1. A method for preparing compounds of formula (I)

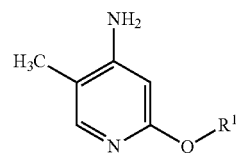

(I)

and/or compounds of formula (II),

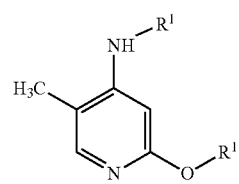

(II)

in which $R^1$ is benzyl, comprising at least the step of reacting a compound of formula (III),

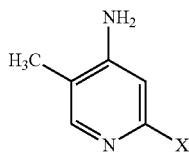

in which X is Cl or Br,
with a compound of formula (IV),

in which the radical $R^1$ has the definition specified for formula (I),
in the presence of a base and a solvent,
wherein the base is selected from alkali metal hydroxides, alkaline earth metal hydroxides, alkali metal carbonates, alkaline earth metal carbonates, compounds of formula (V)

in which the radical $R^1$ has the definition specified for formula (I) and M is an alkali metal, or mixtures thereof,
wherein the solvent is selected from toluene, o-, m-, p-xylene, ethylbenzene, ethoxybenzene, compounds of formula (IV), water, or mixtures thereof, and
wherein the reaction of the compound of formula (III) with the compound of formula (IV) is carried out in the absence of a catalyst selected from transition metal compounds.

2. The method as claimed in claim 1, wherein the reaction is carried out at temperatures of 100° C. to 180° C.

3. The method as claimed in claim 1, wherein 1 to 10 mol of the compound of formula (IV) are used per mole of the compound of formula (III).

4. The method as claimed in claim 1, wherein 1.5 to 6 mol of the base are used per mole of the compound of formula (III).

5. The method as claimed in claim 1, further comprising the steps of
a) providing at least the base,
b) adding the compound of formula (III), without solvent or as a solution, to at least the base of step a) at temperatures of 0 to 170° C., providing a mixture, and
c) reacting the mixture provided in step b) at temperatures of 120 to 170° C.

6. The method as claimed in claim 1, further comprising the steps of
a) providing a mixture of the base and the compound of formula (IV), wherein the base is selected from the group consisting of a compound of formula (V), NaOH, and KOH,
b) adding the compound of formula (III) to the mixture provided in step a) at temperatures of 120 to 170° C., and
c) reacting the mixture provided in step b) at temperatures of 120 to 170° C.

7. The method as claimed in claim 1, wherein at least the base and the compound of formula (III) are mixed and this mixture is heated to 120 to 170° C.

8. The method as claimed in claim 7, wherein the base is selected from a compound of formula (V), NaOH or KOH, and at least the base, the solvent, and the compound of formula (IV) are mixed and this mixture is heated to 120 to 170° C.

9. The method as claimed in claim 1, wherein at least the compound of formula (III) is initially charged and then the base and the compound of formula (IV) is added.

10. The method as claimed in claim 9, wherein at least the compound of formula (III) and the solvent are initially charged and then the base and the compound of formula (IV) are added, wherein the base is a compound of formula (V).

11. The method as claimed in claim 1, wherein a liquid phase is distilled off during the reaction.

* * * * *